United States Patent
Baheti et al.

(10) Patent No.: US 10,300,081 B2
(45) Date of Patent: *May 28, 2019

(54) MODIFIED RELEASE DOXYCYCLINE COMPOSITION

(71) Applicant: Nestle Skin Health SA, Lausanne (CH)

(72) Inventors: Ankit Baheti, Indore (IN); Bijay Kumar Padhi, Ganjam District (IN); Rajeev Singh Raghuvanshi, Gurgaon (IN)

(73) Assignee: NESTLE SKIN HEALTH SA, Lausanne (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/875,369

(22) Filed: Jan. 19, 2018

(65) Prior Publication Data

US 2018/0200272 A1   Jul. 19, 2018

Related U.S. Application Data

(63) Continuation of application No. 15/359,292, filed on Nov. 22, 2016, now Pat. No. 9,901,588, which is a continuation of application No. 14/946,715, filed on Nov. 19, 2015, now Pat. No. 9,532,996.

(30) Foreign Application Priority Data

Nov. 19, 2014   (IN) .......................... 5805/CHE/2014

(51) Int. Cl.
| | | |
|---|---|---|
| *A61K 31/65* | (2006.01) | |
| *A61K 9/00* | (2006.01) | |
| *A61K 9/50* | (2006.01) | |
| *A61K 9/48* | (2006.01) | |

(52) U.S. Cl.
CPC ............ *A61K 31/65* (2013.01); *A61K 9/0053* (2013.01); *A61K 9/4816* (2013.01); *A61K 9/4866* (2013.01); *A61K 9/5078* (2013.01)

(58) Field of Classification Search
CPC ..................................................... A61K 31/65
See application file for complete search history.

(56) References Cited

U.S. PATENT DOCUMENTS

| | | |
|---|---|---|
| 5,084,287 A | 1/1992 | Ghebre-Sellassie et al. |
| 5,167,964 A | 12/1992 | Muhammad et al. |
| 5,188,836 A | 2/1993 | Muhammad et al. |

(Continued)

FOREIGN PATENT DOCUMENTS

| | | |
|---|---|---|
| WO | WO2002083106 | 10/2002 |
| WO | WO2004091483 | 10/2004 |

OTHER PUBLICATIONS

Agwuh et al. "Pharmacokinetics and pharmacodynamics of the tetracyclines including glycylcyclines," Jul. 1, 2006, Journal of Antimicrobial Chemotherapy, vol. 58, No. 2, pp. 256-265.

(Continued)

*Primary Examiner* — San Ming R Hui
(74) *Attorney, Agent, or Firm* — Sunit Talapatra; Foley & Lardner LLP

(57) ABSTRACT

Doxycycline formulations with a reduced food effect are disclosed. Particularly disclosed are modified release formulations which can be administered once a day and exhibit a reduced food effect. Methods of treating inflammatory conductions such as rosacea or inflammatory symptoms such as the papules and pustules of rosacea or acne vulgaris are also disclosed.

9 Claims, 4 Drawing Sheets

(56) References Cited

U.S. PATENT DOCUMENTS

| | | |
|---|---|---|
| 7,211,267 B2 | 5/2007 | Ashley |
| 7,232,572 B2 | 6/2007 | Ashley |
| 7,749,532 B2 | 7/2010 | Chang et al. |
| 8,206,740 B2 | 6/2012 | Chang et al. |
| 8,394,405 B2 | 3/2013 | Chang et al. |
| 8,394,406 B2 | 3/2013 | Chang et al. |
| 8,470,364 B2 | 6/2013 | Chang et al. |
| 8,603,506 B2 | 12/2013 | Ashley |
| 8,652,516 B1 | 2/2014 | Etchegaray et al. |
| 8,709,478 B2 | 4/2014 | Chang et al. |
| 9,132,092 B1 | 9/2015 | Sharma et al. |
| 9,241,946 B2 | 1/2016 | Ashley |
| 9,463,196 B2 | 10/2016 | Sharma et al. |
| 9,561,242 B2 | 2/2017 | Sharma et al. |
| 9,566,287 B2 | 2/2017 | Sharma et al. |
| 2004/0142035 A1 | 7/2004 | Chang et al. |
| 2012/0244216 A1 | 9/2012 | Shah et al. |
| 2014/0271834 A1 | 9/2014 | Etchegaray et al. |
| 2014/0274970 A1 | 9/2014 | Chandran et al. |
| 2015/0057254 A1 | 2/2015 | Chang et al. |
| 2016/0008379 A1 | 1/2016 | Jami et al. |
| 2016/0082021 A1 | 3/2016 | Sharma et al. |
| 2016/0106764 A1 | 4/2016 | Etchegaray et al. |
| 2016/0113880 A1 | 4/2016 | Chang et al. |
| 2016/0143923 A1 | 5/2016 | Fanda et al. |
| 2016/0143924 A1 | 5/2016 | Jami et al. |
| 2016/0151396 A1 | 6/2016 | Sharma et al. |
| 2016/0151397 A1 | 6/2016 | Sharma et al. |
| 2017/0071957 A1 | 3/2017 | Baheti et al. |

OTHER PUBLICATIONS

Partial International Search for Application No. PCT/IB2015/002337 dated Feb. 25, 2016.

Welling et al, "Bioavailability of tetracycline and doxycycline in fasted and nonfasted subjects," Mar. 1977, Antimicrobial agents and chemotherapy, vol. 11, No. 3, pp. 462-469.

International Preliminary Report and Written Opinion for Application No. PCT/IB2015/002337, dated May 23, 2017, 10 pages.

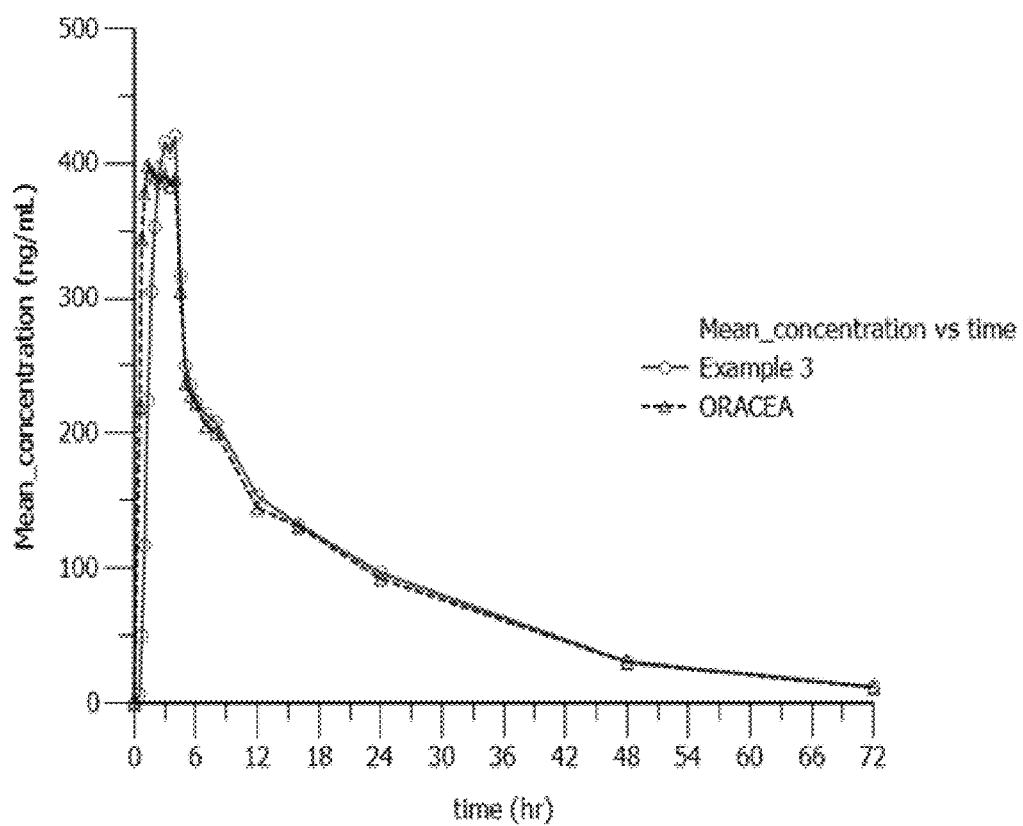

MODIFIED RELEASE DOXYCYCLINE COMPOSITION

CROSS-REFERENCE TO RELATED APPLICATIONS

The present application is a continuation of U.S. patent application Ser. No. 15/359,292, filed Nov. 22, 2016, which is a continuation of U.S. patent application Ser. No. 14/946,715, filed Nov. 19, 2015, now U.S. Pat. No. 9,532,996, which claims the benefit of the filing date of Indian Patent Application No. IN 5805/CHE/2014, filed Nov. 19, 2014, the disclosures of which are hereby incorporated herein by reference.

FIELD OF INVENTION

The present application relates to a modified release composition of doxycycline.

BACKGROUND

Doxycycline is a broad spectrum bacteriostatic compound that is effective against Gram-positive, Gram-negative, aerobic and anaerobic bacteria, as well as spirochetes, mycoplasmas, rickettsiae, chlamydiae and some protozoans. It works by inhibiting protein synthesis in bacteria or protozoans. It is commonly used in the treatment of bacterial infections caused by these organisms, such as urinary tract infections, upper respiratory tract infections, acne, gonorrhea, chlamydia, anthrax, lyme disease and others.

Besides antibiotic activity, doxycycline also has some other mechanism of actions like interfering with the chemotaxis of polymorphonuclear leukocytes (PMN) into the inflammatory lesion, inhibition of PMN derived collagenase, scavenging reactive oxidative species produced by resident inflammatory cells etc. Therefore doxycycline is also being used as an anti-inflammatory to treat inflammatory conditions or symptoms, such as diseases like periodontitis, rosacea and acne. In these instances, it is used in an anti-inflammatory effective amount which, may be lower than traditionally prescribed when doxycycline is used for its antibiotic activity.

Doxycycline as an antibiotic is available in 50 mg, 100 mg, and 200 mg oral doses, whereas as for treating periodontitis and rosacea, lower strengths of 20 mg & 40 mg oral doses are marketed as PERIOSTAT® and ORACEA® respectively. These doses can be given once or more per day as directed by a physician. ORACEA® is a 40 mg dose administered once in a 24 hour period. Sustained release formulations of doxycycline are also described in U.S. Pat. Nos. 5,084,287 and 5,188,836.

Oral administration of drugs is frequently affected by food-drug interactions, a phenomenon often described by the term "food effect". Food effect generally refers to all type of interactions of food with drug which affect its dissolution, absorption, distribution, metabolism and/or elimination. The implications of food effect can, in some instances, include changes in bioavailability, rate of on-set of therapeutic action, duration of therapeutic effect and incidence of side effects.

The food effect is an important issue during the development of a drug. In some cases food-drug interactions lead to an increase of drug absorption and the drug formulation may be recommended to be taken with food in order to be sufficiently absorbed and exert its expected clinical effect. In some other case food interrupts the absorption of active agent and therefore it reduces $C_{max}$ and AUC leading to poor therapeutic effect. In those cases, there may be warnings provided to the user to take the drug, for example, one hour before or two hours after eating.

The food effect on doxycycline pharmacokinetics is well known. Indeed, ORACEA® is reported to have 45% and 22% in $C_{max}$ and AUC respectively (meaning that the $C_{max}$ and AUC of ORACEA® when given in the fed versus fasted state differ by 45% and 22% respectively) and carries the exact dosing restriction noted above.

In addition to its known impact on the gastrointestinal microbiology of a patient, doxycycline is known to have possible adverse gastrological effects which are attributed to irritation of the mucosa. Such effects may include anorexia, nausea, diarrhoea, glossitis, dysphagia, enterocolitis. Further there is huge risk of esophageal irritation and ulceration in patients receiving capsule and tablet forms of the doxycycline, especially when patients immediately go to bed or lie down following dosing, or when the doses are taken without sufficient liquid. Therefore it is necessary the patients should be administered with adequate amounts of fluid or food and the patients are instructed to remain sitting or standing for up to 2 hours post administration to prevent the possible development of oesophageal irritation. Similar restrictions are known for other drug products, like bisphosphonates. These dosing restrictions can understandably cause inconvenience and discomfort to the patients which can impact compliance.

Thus, a need exists to provide a modified release dosage form of doxycycline with reduced or no significant food effect. Further it is desired to have a dosage form of doxycycline which are expected to reduce or prevent risk of esophageal irritation and ulceration in patients and further improves the compliance.

SUMMARY OF THE INVENTION

The present application relates to a modified release composition of doxycycline.

In one embodiment, the present application relates to a modified release composition comprising:
I. doxycycline;
II. one or more water soluble and insoluble polymers; and
III. one or more pharmaceutically acceptable excipients;
wherein said composition when subjected to a changeover dissolution study releases no more than 30% in 30 minutes, in 750 ml of pH 1.2 acidic solution (0.1N HCl); and has at least one of the following release profile in 950 ml of an pH 6.0 phosphate buffer solution:
a. less than about 30% in 35 minutes;
b. less than about 60% in 45 minutes; and
c. more than 85% in 60 minutes In another embodiment, the modified release composition of the present application comprising doxycycline, wherein said composition provides at least one of the following pharmacokinetic parameters:
a. doxycycline plasma concentration of not more than about 50 ng/ml of doxycycline at 30 minutes;
b. doxycycline plasma concentration of not more than about 100 ng/ml of doxycycline at 45 minutes; and
c. doxycycline plasma concentration of not more than about 200 ng/ml of doxycycline at 60 minutes.

In another embodiment, the modified release composition of the present application provides peak plasma concentration from about 200 ng/ml to about 1000 ng/ml of doxycycline at 90 minutes.

In another embodiment, the modified release composition of the present application comprising doxycycline provides at least one of the following pharmacokinetic parameters:
 a. doxycycline plasma concentration of not more than about 15 ng/ml of doxycycline at 30 minutes;
 b. doxycycline plasma concentration of not more than about 60 ng/ml of doxycycline at 45 minutes; and
 c. doxycycline plasma concentration of not more than about 200 ng/ml of doxycycline at 60 minutes.

In another embodiment, the present application relates to a modified release composition for once daily oral administration comprising:
 I. doxycycline,
 II. one or more water soluble and insoluble polymers and
 III. one or more pharmaceutically acceptable excipients, wherein said composition upon oral administration to a human subjects in fasting state provides at least one of the doxycycline plasma concentration parameters:
 a. not more than about 15 ng/ml of doxycycline at 30 minutes;
 b. not more than about 60 ng/ml of doxycycline at 45 minutes; and
 c. not more than about 200 ng/ml of doxycycline at 60 minutes.

In another embodiment, the present application relates to a modified release composition comprising:
 I. doxycycline;
 II. one or more water soluble and insoluble polymers; and
 III. one or more pharmaceutically acceptable excipients; wherein said composition upon oral administration in fasting state exhibits bioequivalence to a commercially available 40 mg doxycycline composition and said bioequivalence is established by:
 a. a 90% Confidence Interval for mean $AUC_{(0-t)}$, which is between 80% and 125%,
 b. a 90% Confidence Interval for mean $AUC_{(0-inf)}$, which is between 80% and 125%, and
 c. a 90% Confidence Interval for mean $C_{max}$, which is between 80% and 125%.

In another embodiment, the present application relates to a modified release composition comprising:
 I. doxycycline,
 II. one or more water soluble and insoluble polymers and
 III. one or more pharmaceutically acceptable excipients, wherein said composition upon oral administration in a fed state exhibits bioequivalence to a commercially available 40 mg doxycycline composition administered in fasting state and said bioequivalence is established by:
 a. a 90% Confidence Interval for mean $AUC_{(0-t)}$, which is between 80% and 125%; and
 b. a 90% Confidence Interval for mean $AUC_{(0-inf)}$, which is between 80% and 125%.
In another aspect of this embodiment the composition is provided as a once a day oral dosage form.

In another embodiment, the present application relates to a modified release composition comprising:
 I. doxycycline;
 II. one or more water soluble and insoluble polymers; and
 III. one or more pharmaceutically acceptable excipients; wherein said composition provides at least one of the following pharmacokinetic parameters:
 a) a fed/fasted ratio for $C_{max}$ in the range of about 0.60 to about 1.00;
 b) a fed/fasted ratio for $AUC_{0-t}$ in the range of about 0.89 to about 1.00; and
 c) a fed/fasted ratio for $AUC_{0-inf}$ in the range of about 0.89 to about 1.00.

In another embodiment, the present application relates to a method of treating rosacea in a human subject in need thereof comprising:
 I. doxycycline,
 II. one or more water soluble and insoluble polymers, and
 III. one or more pharmaceutically acceptable excipients; wherein said composition has reduced food effect.

In another embodiment, the present application relates to a method of treating rosacea or an inflammatory symptom of rosacea or acne vulgaris in a human subject in need thereof comprising:
 I. doxycycline,
 II. one or more water soluble and insoluble polymers and
 III. one or more pharmaceutically acceptable excipients, wherein said composition upon oral administration in a fed state exhibits bioequivalence to a commercially available 40 mg doxycycline composition administered in fasting state and said bioequivalence is established by:
 a. a 90% Confidence Interval for mean $AUC_{(0-t)}$, which is between 80% and 125%; and
 b. a 90% Confidence Interval for mean $AUC_{(0-inf)}$, which is between 80% and 125%.

In another embodiment, the method of treating rosacea or an inflammatory symptom of rosacea or acne vulgaris in a human subject in need thereof comprising orally administering a modified release composition of doxycycline, wherein said composition has reduced food effect.

In another embodiment, the method of treating rosacea or an inflammatory symptom of acne vulgaris in a human subject in need thereof comprising orally administering a modified release composition of doxycycline, wherein said composition has reduced food effect, and said food effect is less than about 40% in $C_{max}$ In another embodiment, the method of treating rosacea or an inflammatory symptom of rosacea or acne vulgaris in a human subject in need thereof comprising orally administering a modified release composition of doxycycline, wherein said composition has reduced food effect, and said food effect is less than about 35% in $C_{max}$ In another embodiment, the method of treating rosacea or an inflammatory symptom of rosacea or acne vulgaris in a human subject in need thereof comprising orally administering a modified release composition of doxycycline, wherein said composition has reduced food effect, and said food effect is less than about 15% in AUC ($AUC_{(0-t)}$ and/or $AUC_{(0-inf)}$).

In another embodiment, the method of treating rosacea or an inflammatory symptom of rosacea or acne vulgaris in a human subject in need thereof comprising orally administering a modified release composition of doxycycline, wherein said composition has reduced food effect, and said food effect is less than about 12% in AUC ($AUC_{(0-t)}$ and/or $AUC_{(0-inf)}$).

In another embodiment, the method of treating rosacea or an inflammatory symptom of rosacea or acne vulgaris in a human subject in need thereof comprising orally administering an once daily modified release composition comprising doxycycline, wherein said composition has reduced food effect and said food effect is lower than the food effect of commercially available 40 mg doxycycline composition by at least 15% in $C_{max}$ and AUC ($AUC_{(0-t)}$ and/or $AUC_{(0-inf)}$)

In another embodiment, the method of treating rosacea or an inflammatory symptom of rosacea or acne vulgaris in a human subject in need thereof comprising orally administering a modified release composition comprising:

I. doxycycline
II. one or more water soluble and insoluble polymers; and
III. one or more pharmaceutically acceptable excipients;
wherein said composition provides at least one of the following pharmacokinetic parameters:
a) a fed/fasted ratio for $C_{max}$ in the range of about 0.60 to about 1.00;
b) a fed/fasted ratio for $AUC_{0-t}$ in the range of about 0.89 to about 1.00; and
c) a fed/fasted ratio for $AUC_{0-inf}$ in the range of about 0.89 to about 1.00.

In another embodiment, the method of treating rosacea or an inflammatory symptom of rosacea or acne vulgaris in a human subject in need thereof comprising orally administering a modified release composition comprising:
I. doxycycline;
II. one or more water soluble and insoluble polymers; and
III. one or more pharmaceutically acceptable excipients;
wherein said composition upon oral administration in fasting state exhibits bioequivalence to a commercially available 40 mg doxycycline composition and said bioequivalence is established by:
a. a 90% Confidence Interval for mean $AUC_{(0-t)}$, which is between 80% and 125%,
b. a 90% Confidence Interval for mean $AUC_{(0-inf)}$, which is between 80% and 125%, and
c. a 90% Confidence Interval for mean $C_{max}$, which is between 80% and 125%.

In another embodiment, the method of treating rosacea or an inflammatory symptom of rosacea or acne vulgaris in a human subject in need thereof comprising orally administering a modified release composition comprising:
I. about 46 mg of doxycycline hyclate;
II. one or more water soluble and insoluble polymers; and
III. one or more pharmaceutically acceptable excipients;
wherein said composition upon oral administration in fasting state exhibits bioequivalence to a commercially available 40 mg doxycycline composition and said bioequivalence is established by:
d. a 90% Confidence Interval for mean $AUC_{(0-t)}$, which is between 80% and 125%,
e. a 90% Confidence Interval for mean $AUC_{(0-inf)}$, which is between 80% and 125%, and
f. a 90% Confidence Interval for mean $C_{max}$, which is between 80% and 125%.

In another embodiment, the present application relates to a modified release composition comprising
I. doxycycline;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and for a time period of $T_{0\ min}$ to $T_{60\ mins}$.

In another embodiment, the modified release composition of the present application comprising
I. doxycycline
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$, wherein said composition provides at least one of the following pharmacokinetic parameters:
a. average input rate of from about 4 ng/hr/ml to about 15 ng/hr/ml during the time period of $T_{0\ min}$ to $T_{30\ mins}$.
b. average input rate of from about 15 ng/hr/ml to about 40 ng/hr/ml during the time period of $T_{0\ min}$ to $T_{60\ mins}$.

In another embodiment, the modified release composition of the present application comprising
I. doxycycline;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$, wherein said composition provides at least one of the following pharmacokinetic parameters:
a. average input rate of from about 5 ng/hr/ml to about 8 ng/hr/ml during the time period of $T_{0\ min}$ to $T_{30\ mins}$.
b. average input rate of from about 15 ng/hr/ml to about 20 ng/hr/ml during the time period of $T_{0\ min}$ to $T_{60\ mins}$.

In another embodiment, the modified release composition comprising
I. doxycycline;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$, wherein said composition has reduced food effect.

In another embodiment, the modified release composition comprising doxycycline has reduced food effect, and said food effect is less than about 40% in $C_{max}$.

In another embodiment, the modified release composition of the present application has reduced food effect, and said food effect is less than about 35% in $C_{max}$.

In another embodiment, the modified release composition comprising doxycycline has reduced food effect, and said food effect is less than about 15% in $AUC_{(0-t)}$.

In another embodiment, the modified release composition comprising doxycycline has reduced food effect, and said food effect is less than about 12% in $AUC_{(0-t)}$.

In another embodiment, the modified release composition comprising doxycycline has reduced food effect, and said food effect is less than about 15% in $AUC_{(0-inf)}$.

In another embodiment, the modified release composition comprising doxycycline has reduced food effect, and said food effect is less than about 12% in $AUC_{(0-inf)}$.

In another embodiment, the modified release composition comprising
I. doxycycline;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$; and
wherein said composition has reduced food effect and said food effect is lower than the food effect of commercially available 40 mg doxycycline composition by at least 15% in $C_{max}$ and AUC ($AUC_{(0-t)}$ and/or $AUC_{(0-inf)}$).

In another embodiment, the modified release composition comprising
I. doxycycline;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$; and
wherein said composition provides at least one of the following pharmacokinetic parameters:
a) a fed/fasted ratio for $C_{max}$ in the range of about 0.60 to about 1.00;
b) a fed/fasted ratio for $AUC_{0-t}$ in the range of about 0.89 to about 1.00; and
c) a fed/fasted ratio for $AUC_{0-inf}$ in the range of about 0.89 to about 1.00.

In another embodiment, the modified release composition comprising
I. doxycycline;
II. one or more water soluble and insoluble polymers; and
III. one or more pharmaceutically acceptable excipients;
wherein said composition has dC/dT value less than 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$; and
wherein said composition upon oral administration in fasting state exhibits bioequivalence to a commercially available 40 mg doxycycline composition and said bioequivalence is established by:
a. a 90% Confidence Interval for mean $AUC_{(0-t)}$, which is between 80% and 125%,
b. a 90% Confidence Interval for mean $AUC_{(0-inf)}$, which is between 80% and 125%, and
c. a 90% Confidence Interval for mean $C_{max}$, which is between 80% and 125%.

In another embodiment, the modified release composition of the present application is orally administered once daily.

In another embodiment, the modified release composition of the present application is orally administered twice daily.

In another embodiment, the modified release composition of the present application is orally administered to human subjects in need thereof.

In another embodiment, the modified release composition of the present application comprises doxycycline, wherein said doxycyline is an acid addition salt of doxycycline. In still another aspect of this embodiment, the doxycycline is administered in an amount of between about 30 and less than 50 mg, based on the weight of doxycycline base, in yet another aspect, between about 35 and about 45 mg, and in yet a further aspect between about 35 and about 40 mg of doxycycline based on the equivalent weight of doxycycline base.

In another embodiment, the modified release composition of the present application comprises doxycycline, which is doxycycline hyclate.

In another embodiment, doxycycline hyclate is present in an amount of about 46 mg.

In another embodiment, doxycycline hyclate is present in an amount of 46.16 mg.

In another embodiment there is provided a method of treating inflammatory rosacea or an inflammatory symptom of either rosacea or acne vulgaris in a human patient in need thereof comprising: administering to said patient a total daily dose of about 35 mg to about 45 mg of a doxycycline hydrate or acid addition salt, based on the equivalent weight of doxycycline base, wherein the total daily dose of doxycycline is provided so as to result in a reduced food effect.

In another aspect of this method the total daily dose is administered once a day and provides a reduced food effect whereby both AUC and a $C_{max}$ are lower than the food effect of commerically available 40 mg doxycycline compositions by at least about 15%.

In another aspect of the method, the total daily dose is administered once a day less than one hour before or less than two hours after a meal.

In another aspect of the method, the total daily dose exhibits a reduced food effect selected from the group consisting of an AUC of less than about 15% and a $C_{max}$ of less than about 40% upon oral administration to a human in a fed state.

In another aspect of the method, upon oral administration in a fasting state the total daily dose exhibits bioequivalence to a commercially available 40 mg doxycycline composition.

In another aspect of the method, bioequivalence is established by:
a. a 90% Confidence Interval for mean $AUC_{(0-t)}$, which is between 80% and 125%,
b. a 90% Confidence Interval for mean $AUC_{(0-\infty)}$, which is between 80% and 125%, and
c. a 90% Confidence Interval for mean $C_{max}$, which is between 80% and 125%.

In another aspect of the method, the acid addition salt is doxycycline hyclate is present in an amount of about 46 mg.

In another aspect of the method, the doxycycline is a hydrate and the hydrate is the monohydrate.

In another aspect of the method, the inflammatory symptom of either rosacea or acne vulgaris is papules and pustules of either rosacea or acne vulgaris.

BRIEF DESCRIPTION OF THE DRAWINGS

FIG. 3 B. shows 72-hour Mean plasma doxycycline concentration—Time profile of Example 3 administered to 52 subjects in fasting state.

DETAILED DESCRIPTION

Definitions

Figure 1:
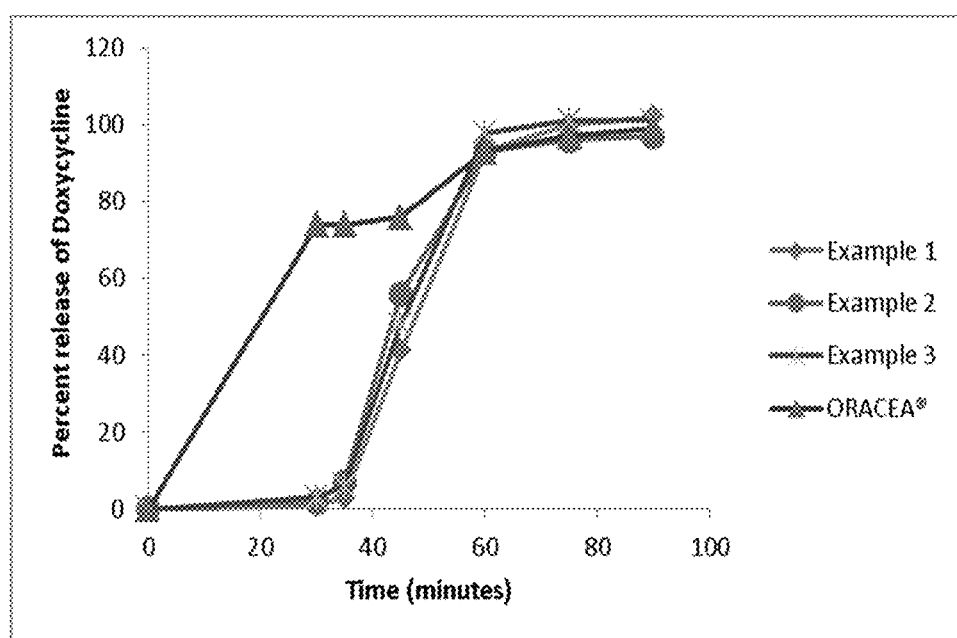
FIG. 1 shows in vitro release profile of Example 1, 2, 3 and ORACEA® in change over media (Acidic medium-pH1.2 and phosphate buffer-pH 6.0).

Unless otherwise defined, all technical and scientific terms used herein have the same meaning as commonly understood by one of ordinary skill in the art.

"Doxycycline" herein refers to any form of doxycycline including hydrates such as doxycycline monohydrate, anhydrous doxycycline, doxycycline base or acid addition salts of doxycycline such as doxycycline hyclate or any other pharmaceutically acceptable salt thereof in an amount of about 30 mg to less than 50 mg of doxycycline base or an equivalent amount of any other form of doxycycline.

In the present application, the amount of doxycycline used may be from about 30 mg to about 45 mg, or from about 35 mg to about 45 mg, or from about 35 mg to about 40 mg, or from about 40 mg to about 45 mg of doxycycline base or an equivalent amount of any other form of doxycycline. For example in the present application, the doxycycline hyclate in an amount of about 46 mg provides about 40 mg of doxycycline base similarly, where it is stated that an amount of or range of one or more forms of doxycycline is "based on the equivalent weight of doxycycline base" or variances thereof, it is meant that the amount of that form or forms of doxycycline will be sufficient to provide an equivalent amount of doxycycline base. Thus, for example, about 35 mg to about 45 mg of doxycycline monohydrate based on the equivalent weight of doxycycline base means enough doxycycline monohydrate so as to provide 35 to 45 mg of doxycycline base. Unless stated otherwise, these doses are the total daily dose. They can be given in a single dosage form or multiple dosage forms, preferably in a single dosage form given once a day.

The amount of doxycycline in certain embodiments thereof is an amount sufficient to provide peak plasma concentration of doxycycline from about 200 ng/ml to about 1000 ng/ml. The amount of doxycycline per unit dosage form used in certain embodiments hereof is an amount sufficient to provide an equivalent of about 30 mg to about 40 mg of doxycycline base per dose per day or that provides peak plasma concentration of doxycycline from about 200 ng/ml to about 1000 ng/ml.

Doxycycline as used herein also encompasses their complexes, polymorphs, hydrates, solvates, enantiomers or racemates. The solid state of doxycycline used in the composition of the present application is not critical. For example, doxycycline can be amorphous or crystalline.

The term "about", as used herein, means within 10% of a given value or range. Alternatively, the term "about" means within an acceptable standard error of the mean as would be appropriate.

The term "food effect", as used herein, refers to relative difference in AUC (area under the curve $AUC_{(0-t)}$ and/or $AUC_{(0-\infty)}$,) or $C_{max}$ (maximum plasma concentration or peak plasma concentration) of an active substance, when said substance or a composition thereof, such as a tablet or a capsule, is administered orally to a subject, concomitantly with food or in a fed state as compared to the same values when the same substance or a composition thereof is administered in a fasted state.

The food effect F is calculated as $$F \% = \frac{(X_{fasted} - X_{fed})}{X_{fasted}} \times 100$$

wherein $X_{fed}$ and $X_{fasted}$ are the values of AUC ($AUC_{(0-t)}$ and/or $AUC_{(0-\infty)}$) or $C_{max}$ in the fed and fasted state, respectively.

The term "reduced food effect", as used herein, refers to the food effect in AUC ($AUC_{(0-t)}$ and/or $AUC_{(0-\infty)}$) and $C_{max}$ of a composition of doxycycline is less than about 15% and 40% respectively. In $C_{max}$, "reduced food effect" refers to food effect in $C_{max}$ of a composition of doxycycline and is at least less than about 40%. In AUC, "reduced food effect" refers to food effect in AUC ($AUC_{(0-t)}$ and/or $AUC_{(0-\infty)}$) of a composition of doxycycline and is at least less than about 15%. In another embodiment, the reduced food effect is less than about 35% in terms of $C_{max}$ or less than about 12% in terms of AUC. In still another embodiment both AUC and $C_{max}$ are lower than the food effect of commerically available 40 mg doxycycline compositions as defined herein by at least about 15%.

Indeed, because of the reduced food effect of the present invention particularly when compared to commercial products such as ORACEA®, it is possible to administer doxycycline to treat inflammatory conditions or symptoms of inflammatory conditions (for example, the papules and pustules of acne vulgaris or rosacea) with a reduced food effect. In some embodiments this may be accomplished without need for normal administration warnings and/or without requiring the patient be in a fasted state. Because of this, the patient may take their doxycycline dose even less than an hour before a meal, or two hours after a meal or otherwise in the fed state.

The term "dC/dT" as used herein, refers to change in doxycycline concentration in plasma as a function of time or change in plasma concentration of doxycycline during the said time period or interval.

It is calculated as $$dC/dT = \frac{(\text{Plasma Concentration}_{T2} - \text{Plasma Concentration}_{T1})}{(\text{Time point}_2 - \text{Time point}_1)}$$

The term "modified release composition" herein refers to any composition or dosage form which comprises an active drug and which is formulated to provide a longer duration of pharmacological response after administration of the dosage form than is ordinarily experienced after administration of a corresponding immediate release composition comprising the same drug in the same amount. Modified release compositions include, inter alia, those compositions described elsewhere as "controlled release", "extended release", "delayed release", "sustained release", "prolonged release", "programmed release", "time release" and/or "rate controlled" compositions or dosage forms.

As used herein, the terms "composition" and "formulation" are used interchangeably and refer to a mixture of two or more compounds, elements, or molecules. Also the terms "composition" and "formulation" may be used to refer to a mixture of one or more active agents with a carrier or other excipients. Furthermore, the term "dosage form" can include one or more composition(s) or formulation(s) provided in a format for administration to a patient in need thereof.

The term "Changeover dissolution study" herein refers to a dissolution study performed by using USP apparatus I (Basket) with 50 rpm and the dissolution methodology includes two stages i.e., acid stage followed by buffer stage. Firstly in vitro dissolution was carried out in acid stage pH 1.2 (750 ml of 0.1N HCl solution, USP Type 1 apparatus at a speed of 50 rpm and 37° C.) till 30 minutes and after 30 minutes the study was continued in buffer stage (950 ml of phosphate buffer solution (pH 6.0), USP Type 1 apparatus at a speed of 50 rpm and 37° C.). As used herein, the term "commercially available 40 mg doxycycline composition" refers to ORACEA® oral capsules containing doxycycline, USP in an amount equivalent to 40 mg of anhydrous doxycycline, marketed by Galderma Laboratories, L.P Further Embodiments The present application relates to a modified release composition doxycycline.

In another embodiment, the present application relates to a modified release composition comprising:
I. doxycycline;
II. one or more water soluble and insoluble polymers; and
III. one or more pharmaceutically acceptable excipients;
wherein said composition when subjected to a changeover dissolution study releases no more than 20% in 30 minutes, in 750 ml of pH 1.2 acidic solution (0.1N HCl); and have at least one of the following release profile in 950 ml of an pH 6.0 phosphate buffer solution:
a. less than about 30% in 35 minutes;
b. less than about 60% in 45 minutes; and
c. more than 85% in 60 minutes.

In another embodiment, the present application relates to a modified release composition comprising:
I. doxycycline;
II. one or more water soluble and insoluble polymers; and
III. one or more pharmaceutically acceptable excipients;
wherein said composition when subjected to a changeover dissolution study releases no more than 10% in 30 minutes, in 750 ml of pH 1.2 acidic solution (0.1N HCl); and have at least one of the following release profile in 950 ml of an pH 6.0 phosphate buffer solution:
a. less than about 30% in 35 minutes;
b. less than about 60% in 45 minutes; and
c. more than 85% in 60 minutes.

In another embodiment, the present application relates to a modified release composition comprising:
I. about 46 mg of doxycycline hyclate;
II. one or more water soluble and insoluble polymers; and
III. one or more pharmaceutically acceptable excipients;
wherein said composition when subjected to a changeover dissolution study releases no more than 30% in 30 minutes, in 750 ml of pH 1.2 acidic solution (0.1N HCl); and have at least one of the following release profile in 950 ml of an pH 6.0 phosphate buffer solution:
a. less than about 30% in 35 minutes;
b. less than about 60% in 45 minutes; and
c. more than 85% in 60 minutes.

In another embodiment, the present application relates to a modified release composition comprising:
I. about 46 mg of doxycycline hyclate;
II. one or more water soluble and insoluble polymers; and
III. one or more pharmaceutically acceptable excipients;
wherein said composition when subjected to a changeover dissolution study releases no more than 30% in 30 minutes, in 750 ml of pH 1.2 acidic solution (0.1N HCl); and have at least one of the following release profile in 950 ml of an pH 6.0 phosphate buffer solution:
d. less than about 30% in 35 minutes;
e. less than about 60% in 45 minutes;
f. more than 85% in 60 minutes;
and wherein said composition upon oral administration to a human subjects in fasting state provides at least one of the following pharmacokinetic parameters:
a. doxycycline plasma concentration of not more than about 15 ng/ml of doxycycline at 30 minutes;
b. doxycycline plasma concentration of not more than about 60 ng/ml of doxycycline at 45 minutes;
c. doxycycline plasma concentration of not more than about 200 ng/ml of doxycycline at 60 minutes; and
d. doxycycline plasma concentration from about 200 ng/ml to about 1000 ng/ml of doxycycline at above 90 minutes.

In another embodiment, the present application relates to a modified release composition comprising:
I. about 46 mg of doxycycline hyclate;
II. one or more water soluble and insoluble polymers; and
III. one or more pharmaceutically acceptable excipients;
wherein said composition when subjected to a changeover dissolution study releases no more than 30% in 30 minutes, in 750 ml of pH 1.2 acidic solution (0.1N HCl); and have at least one of the following release profile in 950 ml of an pH 6.0 phosphate buffer solution:
(a) less than about 30% in 35 minutes;
(b) less than about 60% in 45 minutes; and
(c) more than 85% in 60 minutes;
and wherein said composition upon oral administration in fasting state exhibits bioequivalence to a commercially available 40 mg doxycycline composition administered in fasting state and said bioequivalence is established by:
a. a 90% Confidence Interval for mean $AUC_{(0-t)}$, which is between 80% and 125%,
b. a 90% Confidence Interval for mean $AUC_{(0-inf)}$, which is between 80% and 125%, and
c. a 90% Confidence Interval for mean $C_{max}$, which is between 80% and 125%.

In another embodiment, the present application relates to a modified release composition comprising:
I. about 46 mg of doxycycline hyclate;
II. one or more water soluble and insoluble polymers; and
III. one or more pharmaceutically acceptable excipients;
wherein said composition when subjected to a changeover dissolution study releases no more than 30% in 30 minutes, in 750 ml of pH 1.2 acidic solution (0.1N HCl); and have at least one of the following release profile in 950 ml of an pH 6.0 phosphate buffer solution:
a. less than about 30% in 35 minutes;
b. less than about 60% in 45 minutes; and
c. more than 85% in 60 minutes;
and wherein said composition upon oral administration in a fed state exhibits bioequivalence to a commercially available 40 mg doxycycline composition administered in fasting state and said bioequivalence is established by:
a. a 90% Confidence Interval for mean $AUC_{(0-t)}$, which is between 80% and 125%; and
b. a 90% Confidence Interval for mean $AUC_{(0-inf)}$, which is between 80% and 125%.

In another embodiment, the modified release composition of doxycycline as per present application is used for the treatment of rosacea in human subjects in need thereof.

In general the primary signs of rosacea are papules, pustules, flushing, persistent redness, visible blood vessels, bumps and pimples.

There are four subtypes of rosacea:
Subtype 1 (erythematotelangiectatic rosacea), characterized by flushing and persistent redness, and may also include visible blood vessels.
Subtype 2 (papulopustular rosacea), characterized by persistent redness with transient bumps and pimples.
Subtype 3 (phymatous rosacea), characterized by skin thickening, often resulting in an enlargement of the nose from excess tissue, and
Subtype 4 (ocular rosacea), characterized by ocular manifestations such as dry eye, tearing and burning, swollen eyelids, recurrent styles and potential vision loss from corneal damage.

In another embodiment, the modified composition of doxycycline as per present application is used for treating diseases or conditions in which collagenase is produced in excessive amounts causing pathological destruction of tissues, such as periodontal disease, rheumatoid arthritis, hyperparathyroidism, diabetes and acne.

In another embodiment, the present application relates to a method of treating rosacea in a human subject in need thereof comprising:
 I. doxycycline,
 II. one or more water soluble and insoluble polymers, and
 III. one or more pharmaceutically acceptable excipients;
 wherein said composition has reduced food effect, and said food effect is less than about 35% in $C_{max}$; and
 wherein said composition upon oral administration in a fed state exhibits bioequivalence to a commercially available 40 mg doxycycline composition administered in fasting state and said bioequivalence is established by:
  a. a 90% Confidence Interval for mean $AUC_{(0-t)}$, which is between 80% and 125%; and
  b. a 90% Confidence Interval for mean $AUC_{(0-inf)}$, which is between 80% and 125%.

In another embodiment, the present application relates to a method of treating rosacea in a human subject in need thereof comprising:
 I. about 46 mg of doxycycline hyclate,
 II. one or more water soluble and insoluble polymers, and
 III. one or more pharmaceutically acceptable excipients;
 wherein said composition has reduced food effect, and said food effect is less than about 35% in $C_{max}$; and
 wherein said composition upon oral administration in a fed state exhibits bioequivalence to a commercially available 40 mg doxycycline composition administered in fasting state and said bioequivalence is established by:
  c. a 90% Confidence Interval for mean $AUC_{(0-t)}$, which is between 80% and 125%; and
  d. a 90% Confidence Interval for mean $AUC_{(0-inf)}$, which is between 80% and 125%.

In another embodiment, the modified release composition comprising doxycycline has reduced food effect and said food effect is at least 15% lower compared to the food effect of commercially available 40 mg doxycycline composition in $C_{max}$ and AUC ($AUC_{(0-t)}$ and/or $AUC_{(0-inf)}$).

In another embodiment, the modified release composition comprising doxycycline has reduced food effect and said food effect is at least 20% lower compared to the food effect of commercially available 40 mg doxycycline composition in $C_{max}$ and AUC ($AUC_{(0-t)}$ and/or $AUC_{(0-inf)}$).

In another embodiment, the modified release composition comprising doxycycline, has reduced food effect and said food effect is at least 30% lower compared to the food effect of commercially available 40 mg doxycycline composition in $C_{max}$ and AUC ($AUC_{(0-t)}$ and/or $AUC_{(0-inf)}$).

In another embodiment, the modified release composition comprising doxycycline has reduced food effect in AUC and said food effect in AUC is at least 40% lower compared to the food effect in AUC of commercially available 40 mg doxycycline composition in AUC ($AUC_{(0-t)}$ and/or $AUC_{(0-inf)}$).

In another embodiment, the modified release composition comprising doxycycline has reduced food effect in AUC and said food effect in AUC is at least 50% lower compared to the food effect in AUC of commercially available 40 mg doxycycline composition in AUC ($AUC_{(0-t)}$ and/or $AUC_{(0-inf)}$).

In another embodiment, the present application relates to a method of treating rosacea in a human subject in need thereof comprising:
 I. doxycycline;
 II. one or more water soluble and insoluble polymers; and
 III. one or more pharmaceutically acceptable excipients;
 wherein said composition has no food effect established by following parameters:
  (a) a 90% Confidence Interval for mean $AUC_{(0-t)}$ of the composition administered under fed state to human subjects is within 80.00% to 125.00% of a $AUC_{(0-t)}$ of the composition administered to human subjects in a fasting state; and
  (b) a 90% Confidence Interval for mean $AUC_{(0-inf)}$ of the composition administered under fed state to human subjects is within 80.00% to 125.00% of a $AUC_{(0-inf)}$ of the composition administered to human subjects in a fasting state.

In another embodiment, the present application relates to a method of treating rosacea in a human subject in need thereof comprising:
 I. about 46 mg of doxycycline hyclate,
 II. one or more water soluble and insoluble polymers, and
 III. one or more pharmaceutically acceptable excipients;
 wherein said composition has no food effect established by following parameters:
  (a) a 90% Confidence Interval for mean $AUC_{(0-t)}$ of the composition administered under fed state to human subjects is within 80.00% to 125.00% of a $AUC_{(0-t)}$ of the composition administered to human subjects in a fasting state; and
  (b) a 90% Confidence Interval for mean $AUC_{(0-inf)}$ of the composition administered under fed state to human subjects is within 80.00% to 125.00% of a $AUC_{(0-inf)}$ of the composition administered to human subjects in a fasting state.

In another embodiment, the present application relates to a method of treating rosacea in a human subject in need thereof comprising:
 I. about 46 mg of doxycycline hyclate,
 II. one or more water soluble and insoluble polymers, and
 III. one or more pharmaceutically acceptable excipients;
 wherein said composition has reduced food effect; and
 wherein said composition upon oral administration in a fasting state provides at least one of the following pharmacokinetic parameters:
  a. doxycycline plasma concentration of not more than about 15 ng/ml of doxycycline at 30 minutes;
  b. doxycycline plasma concentration of not more than about 60 ng/ml of doxycycline at 45 minutes;
  c. doxycycline plasma concentration of not more than about 200 ng/ml of doxycycline at 60 minutes; and
  d. doxycycline plasma concentration from about 200 ng/ml to about 1000 ng/ml of doxycycline at above 90 minutes.

In another embodiment, the present application relates to a method of treating or preventing rosacea in a patient known or suspected to be in need of such treatment or prevention comprising administering to the patient a modified release composition for once daily oral administration in a human subject in need thereof comprising
 I. about 46 mg of doxycycline hyclate;
 II. one or more water soluble and insoluble polymers; and
 III. one or more pharmaceutically acceptable excipients;
 wherein said composition has dC/dT value less than about 80% of the dC/dT value provided by the commercially available 40 mg doxycycline composition, and said dC/dT is measured in a single dose human pharmacokinetic study in fasting state and in a time period of $T_{0\ min}$ to $T_{60\ mins}$.

The AUC data from a food-effect study involving administration of modified release composition comprising doxycycline of present application under fasting state and fed state (with a high-fat meal) provides exposure to the doxycycline and wherein the exposure of doxycycline is not affected by food. Therefore the modified release composition of present application can be taken without regard to meals.

The AUC data from a food-effect study involving administration of modified release composition comprising doxycycline of present application under fasting state and fed state (with meal) provides exposure to the doxycycline and wherein the exposure of doxycycline is not affected by food. Therefore the modified release composition of present application could be taken without regard to meals.

In another embodiment, administration of the modified release composition for once daily oral administration comprising doxycycline to human subjects in need thereof of present application may not require administration of adequate amounts of fluid along with the said composition to wash down the composition to reduce the risk of esophageal irritation and ulceration.

In another embodiment, the present application relates to a modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$.

In some aspects, the modified release composition comprising about 46 mg of doxycycline hyclate has dC/dT value less than about 70% of the dC/dT value provided by the commercially available 40 mg doxycycline composition, and said dC/dT value is measured in a single dose human pharmacokinetic study in a fasting state and in time period of $T_{0\ min}$ to $T_{60\ mins}$.

In some aspects, the modified release composition comprising about 46 mg of doxycycline hyclate has dC/dT value less than about 60% of the dC/dT value provided by the commercially available 40 mg doxycycline composition, and said dC/dT value is measured in a single dose human pharmacokinetic study in fasting state and in a time period of $T_{0\ min}$ to $T_{60\ mins}$.

In some aspects, the modified release composition for once daily oral administration in a human subject in need thereof comprising about 46 mg of doxycycline hyclate has dC/dT value less than 50% of the dC/dT value provided by the commercially available 40 mg doxycycline composition, and said dC/dT value is measured in a single dose human pharmacokinetic study in fasting state and in a time period of $T_{0\ min}$ to $T_{60\ mins}$.

In some aspects, the modified release composition comprising about 46 mg of doxycycline hyclate has dC/dT value less than about 40% of the dC/dT value provided by the commercially available 40 mg doxycycline composition, and said dC/dT value is measured in a single dose human pharmacokinetic study in fasting state and in a time period of $T_{0\ min}$ to $T_{60\ mins}$.

In another embodiment, the modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$; and wherein said composition has reduced food effect.

In another embodiment, the modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$; and wherein said composition has reduced food effect, and said food effect is less than about 35% in $C_{max}$.

In another embodiment, the modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$; and wherein said composition has reduced food effect, and said food effect is less than about 15% in AUC.

In another embodiment, the modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$; and wherein said composition has reduced food effect, and said food effect is less than about 12% in $AUC_{(0-t)}$.

In another embodiment, the modified release composition comprising
I. about 46 mg of doxycycline hyclate;
II. one or more water soluble and insoluble polymers; and
III. one or more pharmaceutically acceptable excipients;
wherein said composition has dC/dT value less than about 80% of the dC/dT value provided by the commercially available 40 mg doxycycline composition, and said dC/dT value is measured in a single dose human pharmacokinetic study in a fasting state and in a time period of $T_{0\ min}$ to $T_{60\ min}$; and wherein said composition has reduced food effect, and said food effect is less than about 12% in $AUC_{(0-inf)}$.

In another embodiment, the modified release composition comprising doxycycline, wherein said composition has reduced food effect and said food effect in $C_{max}$ is lower than the food effect in $C_{max}$ of commercially available 40 mg doxycycline composition by at least 15%.

In another embodiment, the modified release composition comprising doxycycline, wherein said composition has reduced food effect and said food effect in AUC is lower than the food effect in AUC of commercially available 40 mg doxycycline composition by at least 15%.

In another embodiment, the modified release composition comprising doxycycline, wherein food effect of said composition is at least 15% lower compared to the food effect of commercially available 40 mg doxycycline composition.

In another embodiment, the present application relates to a modified release composition comprising
- I. about 46 mg of doxycycline hyclate;
- II. one or more water soluble and insoluble polymers; and
- III. one or more pharmaceutically acceptable excipients;
  wherein said composition has dC/dT value less than 80% of the dC/dT value provided by the commercially available 40 mg doxycycline composition, and said dC/dT value is measured in a single dose human pharmacokinetic study in a fasting state and in a time period of $T_{0\ min}$ to $T_{60\ mins}$;
  and wherein said composition provides $C_{max}$ from about 200 ng/ml to about 1000 ng/ml.

In another embodiment, the present application relates to a modified release composition comprising
- I. about 46 mg of doxycycline hyclate;
- II. one or more water soluble and insoluble polymers; and
- III. one or more pharmaceutically acceptable excipients;
  wherein said composition has dC/dT value less than about 80% of the dC/dT value provided by the commercially available 40 mg doxycycline composition, and said dC/dT value is measured in a single dose human pharmacokinetic study in fasting state and in a time period of $T_{0\ min}$ to $T_{60\ mins}$; and
  wherein said composition provides at least one of the following pharmacokinetic parameters:
  - a. average input rate of from about 5 ng/hr/ml to about 8 ng/hr/ml during the time period of $T_{0\ min}$ to $T_{30\ mins}$.
  - b. average input rate of from about 15 ng/hr/ml to about 20 ng/hr/ml during the time period of $T_{0\ min}$ to $T_{60\ mins}$.

In another embodiment, the modified release composition comprising (i) about 46 mg of doxycycline hyclate, (ii) one or more water soluble and insoluble polymers and (iii) one or more pharmaceutically acceptable excipients, wherein said composition when administered to a human subject under fasting state provides average input rate of about 5 ng/hr/ml to 8 ng/hr/ml during the time period of $T_{0\ mins}$ to $T_{30\ mins}$.

In another embodiment, the modified release composition comprising (i) about 46 mg of doxycycline hyclate, (ii) one or more water soluble and insoluble polymers and (iii) one or more pharmaceutically acceptable excipients, wherein said composition when administered to a human subject under fasting state provides average input rate of about 15 ng/hr/ml to 20 ng/hr/ml during the time period of $T_{0\ min}$ to $T_{60\ mins}$.

In another embodiment, the modified release composition comprising
- I. about 46 mg of doxycycline hyclate;
- II. one or more water soluble and insoluble polymers; and
- III. one or more pharmaceutically acceptable excipients;
  wherein said composition has dC/dT value less than about 80% of the dC/dT value provided by the commercially available 40 mg doxycycline composition, and said dC/dT is measured in a single dose human pharmacokinetic study in a fasting state and in a time period of $T_{0\ min}$ to $T_{60\ mins}$; and
  wherein said composition upon oral administration in fasting state exhibits bioequivalence to a commercially available 40 mg doxycycline composition administered in fasting state and said bioequivalence is established by:
  - a. a 90% Confidence Interval for mean $AUC_{(0-t)}$, which is between 80% and 125%,
  - b. a 90% Confidence Interval for mean $AUC_{(0-inf)}$, which is between 80% and 125%, and
  - c. a 90% Confidence Interval for mean $C_{max}$, which is between 80% and 125%.

In another embodiment, the modified release composition for once daily oral administration in a human subject in need thereof comprising
- I. about 46 mg of doxycycline hyclate;
- II. one or more water soluble and insoluble polymers; and
- III. one or more pharmaceutically acceptable excipients;
  wherein said composition has dC/dT value less than about 80% of the dC/dT value provided by the commercially available 40 mg doxycycline composition, and said dC/dT is measured in a single dose human pharmacokinetic study in a fasting state and in a time period of $T_{0\ min}$ to $T_{60\ mins}$; and
  wherein said composition upon oral administration in a fed state exhibits bioequivalence to a commercially available 40 mg doxycycline composition administered in fasting state and said bioequivalence is established by:
  - a. a 90% Confidence Interval for mean $AUC_{(0-t)}$, which is between 80% and 125%; and
  - b. a 90% Confidence Interval for mean $AUC_{(0-inf)}$, which is between 80% and 125%.

In another embodiment, the modified release composition of the present application is orally administered once daily.

In another embodiment, the modified release composition of the present application is orally administered twice daily.

In another embodiment, the modified release composition of the present application is orally administered to human subjects in need thereof.

In another embodiment, the modified release composition of the present application comprises doxycycline, wherein said doxycyline is an acid addition salt of doxycycline. In still another aspect of this embodiment, the doxycycline is administered in an amount of between about 30 and less than 50 mg, based on the weight of doxycycline base, in yet another aspect, between about 35 and about 45 mg, and in yet a further aspect between about 35 and about 40 mg of doxycycline base on the weight of doxycycline base.

In another embodiment, the modified release composition of the present application comprises doxycycline, which is doxycycline hyclate.

In another embodiment, doxycycline hyclate is present in an amount of about 46 mg.

In another embodiment, doxycycline hyclate is present in an amount of 46.16 mg.

In another embodiment, the present application relates to a modified release composition comprising (i) doxycycline hyclate, (ii) one or more water soluble and insoluble polymers and (iii) other pharmaceutically acceptable excipients.

In another embodiment, the present application relates to a modified release composition of doxycycline for once daily administration, wherein the said composition comprises of (i) one or more core consisting of doxycycline, (ii) a release layer containing one or more water soluble and insoluble polymers over the core and (iii) one or more pharmaceutically acceptable excipients.

In another embodiment, the present application relates to a modified release composition of doxycycline for once daily administration, wherein the said composition comprises of core consisting of about 15-20% w/w of doxycycline, about 10-18% w/w one or more water soluble and insoluble polymers and 1-20% of pharmaceutically acceptable excipients, based on the total weight of the final composition.

In another embodiment, the present application relates to a modified release composition of doxycycline for once daily administration, wherein the said composition comprises of core consisting of about 15-20% w/w of doxycycline hyclate, about 10-18% w/w one or more water soluble and insoluble polymers and 1-20% of pharmaceutically acceptable excipients, based on the total weight of the said composition.

In another embodiment, the present application relates to a modified release composition of doxycycline for once daily oral administration comprising one or more core comprising of about 15-20 % w/w of doxycycline hyclate and the core is further coated by release layer consisting of from about 10-18% w/w one or more water soluble and insoluble polymers.

In one aspect the release layer release comprises a mixture of at least one water soluble polymer and at least one water insoluble polymer.

In another aspect, the release layer comprises of from about 5% w/w to about 40% w/w of water insoluble polymer and from about 2% w/w to 20% w/w of water soluble polymer, based on total weight of the said composition.

In another aspect, the release layer comprises of from about 5% w/w to about 40% w/w of water insoluble polymer and from about 5% w/w to 15% w/w of water soluble polymer, based on total weight of the said composition.

In another aspect, the release layer release comprises a mixture of at least one water soluble polymer and at least one water insoluble polymer and wherein the release layer has a thickness of not more than 500 μm.

In an aspect, the water insoluble polymer can be selected from the group of pH-dependent polymer, hydrophobic polymer, hydrophobic swellable polymer, hydrophobic non-swellable polymers or mixtures thereof.

Examples of water insoluble polymer includes but not limited to poly methacrylic acid derivatives, cellulose derivatives, acrylic acid derivatives, maleic acid copolymers, polyvinyl derivatives, Cellulose based pH dependent release retardant polymers include hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose acetate trimelliate cellulose benzoate phthalate, cellulose propionate phthalate, methylcellulose phthalate, carboxymethylethylcellulose phthalate, ethylhydroxyethylcellulose phthalate and the like, acrylic copolymer based pH dependent release retardant include styrene, acrylic acid copolymer, methyl acrylate, acrylic acid copolymer, methyl acrylate, methacrylic acid copolymer, butyl acrylate, methacrylic acid, methyl methacrylate copolymer (e.g. Trade-names: Eudragit L 100 and Eudragit S, available from Rohm Pharma), ethyl acrylate copolymer (e.g. Trade-name: Eudragit L 100-55, available from Rohm Pharma), octyl acrylate copolymer, Maleic copolymer based pH dependent release retardant include vinylacetate, maleic acid anhydride copolymer, styrene, maleic acid anhydride copolymer, styrene, maleic acid monoester copolymer, vinylmethylether, maleic acid anhydride copolymer, ethylene, maleic acid anhydride copolymer, vinylbutylether, maleic acid anhydride copolymer, acrylonitrile, methyl acrylate, maleic acid anhydride copolymer, butyl acrylate, styrene, maleic acid anhydride copolymer and the like, Polyvinyl derivative based pH dependent release retardant includes polyvinyl alcohol phthalate, polyvinylacetal phthalate, polyvinyl butylate phthalate, polyvinylacetoacetal phthalate and the like. Among these examples, methacrylic acid, methylmethacrylate copolymer and methacrylic acid, ethylacrylate copolymer are are available under the brand name Eudragit®.

In another aspect, the water soluble polymer can be selected from the group of hydrophillic polymer, hydrophillic swellable polymers, or hydrophillic non-swellable polymer or mixtures thereof.

Examples of water soluble polymers include, but not limited to, alkylcelluloses such as methylcellulose; hydroxyalkylcelluloses, for example, hydroxymethyl cellulose, hydroxypropylmethyl cellulose, hydroxyethyl cellulose, hydroxypropyl cellulose and hydroxybutylcellulose; carboxyalkylcelluloses such as carboxymethylcellulose; alKali metal salts of carboxyalkylcelluloses such as sodium carboxymethylcellulose; carboxyalkyl alkylcelluloses such, carboxyalkylcellulose esters; other natural, semi-synthetic, or synthetic polysaccharides such as alginic acid, alkali metal and ammonium salts thereof, carrageenans, galactomannans, tragacanth, agar-agar, gum arabic, guar gum, xanthan gum, starches, pectins, such as sodium carboxymethyl amylopectin, chitin derivates such as chitosan, polyfructans, inulin, sugars, lactose, sucrose, fructose, mannitol, polyvinylalcohol, polyvinylpyrrolidone, polyalkylene oxides such as polyethylene oxide and polypropylene oxide and copolymers of ethylene oxide and propylene oxide, and other materials known to one of ordinary skill in the art.

In another embodiment, the core comprises doxycycline and additionally one or more pharmaceutically acceptable excipients.

In some aspects, the inert core comprises at least one pharmaceutically acceptable excipient selected from the group consisting of: water soluble, water insoluble, water swellable or water non swellable material. For example, the core may comprise one or more of non-pareil seeds, pellets, beads, granules, mini-tablets or a micro-tablet or a microcapsule, or a millisphere, or a nanocapsule, or a nanosphere, or a microsphere. The non-pareil seeds may be made up of any pharmaceutically acceptable excipients such as starch, sugar, microcrystalline cellulose, inorganic salts like crystal sodium chloride, vegetable gums, waxes, and the like. The core may be readily available granulated products such as the spherical granulation product of crystalline cellulose (trade name: AVICEL® SP), the spherical granulation product of crystalline cellulose and lactose (trade name: NONPAREIL® NP-5 and NP-7), the spherical granulation product of refined sucrose (trade name: NONPAREIL®-103), and the spherical granulation product of lactose and alpha-converted starch. The core may also be prepared with the techniques known to a person skilled in the art, such as direct compression, wet granulation, dry granulation, or extrusion-spheronization and the like.

In another embodiment, the active ingredient layer comprises doxycycline, one or more hydrophilic polymer, or other pharmaceutically acceptable excipients. In certain embodiment, there may be one or more layers of active ingredients layer comprising doxycycline. The core may consist of alternate layers of active ingredient and release layer coat.

In another embodiment, the present application relates to a modified release composition for once daily oral administration that can be provided as granules or pellets filled in capsule or sachets or the said composition can be compressed to form a tablet.

In another embodiment, the oral once daily composition of doxycycline as per present application can be provided as granules or pellets which can be sprinkled on food.

In some aspects, in the pharmaceutical compositions described herein having one or more excipients can perform more than one function. All excipients can be used at levels well known to the persons skilled in the art and within the acceptable limits.

In another embodiment, the modified compositions of doxycycline as described herein may comprise one or more pharmaceutically acceptable excipients selected from diluent, disintegrant, binder, lubricant, glidant, plasticizer, anti-tacking agent, opacifying agent, and the like.

Suitable diluents may include one or more of microcrystalline cellulose, starch, dibasic calcium phosphate, tribasic calcium phosphate, calcium carbonate, dextrose, kaolin, magnesium carbonate, magnesium oxide; sugars such as lactose or sucrose; sugar alcohols such as mannitol, sorbitol or erythritol; or mixtures thereof.

Suitable anti-tacking agents, lubricants or glidants may include one or more of talc, metallic stearates such as magnesium stearate, calcium stearate, zinc stearate; colloidal silicon dioxide, finely divided silicon dioxide, stearic acid, hydrogenated vegetable oil, glyceryl palmitostearate, glyceryl monostearate, glyceryl behenate, polyethylene glycols, powdered cellulose, starch, sodium stearyl fumarate, sodium benzoate, mineral oil, magnesium trisilicate, Kaolin; or mixtures thereof. The anti-tacking agent, lubricant or glidant may be used interchangeably.

In one aspect, the compositions of the present application comprising doxycycline, wherein said composition is dispensed in HPMC capsules.

In another aspect, the compositions of the present application comprising doxycycline, can be dispensed in capsules containing not more than 2% w/w of gelatin.

In another embodiment, the present application relates to a modified release composition for once daily oral administration to a human in need thereof comprising doxycycline dispensed in HPMC capsules that yields no more than 1% of hydrolytic impurity such as 4-epidoxycycline, when tested in 45° C. and 75% relative humidity for 24 hrs.

In another embodiment, the present application relates to a process of preparing a modified release composition for once daily oral administration to a human in need thereof comprising the steps of:
a) preparing doxycline solution comprising of doxycycline, one or more hydrophilic polymer, or other pharmaceutically acceptable excipients,
b) layering the doxycycline solution of step a) over the inert cores,
c) coating the cores of step b) with one or more water soluble and insoluble polymers,
d) lubricating the coated cores of step c) and
e) filling of cores of step d) in capsules or in sachets or compressing into tablets.

All the layers, i.e. drug layer or the polymer layers, may be applied as solution/dispersion of coating ingredients using any conventional technique known in the art such as spray coating in a conventional coating pan or fluidized bed processor or dip coating.

The present application is further illustrated by the examples which are provided merely to be exemplary of the composition described above and do not limit the scope of the application. Certain modifications and equivalents will be apparent to those skilled in the art and are intended to be included within the scope of the present application.

EXAMPLES

Examples 1 to Examples 3 illustrates the preparation of doxycycline hyclate modified release dosage form, equivalent to 40 mg of doxycycline base.

Example 1

TABLE 1

| Ingredients | Quantity per Unit (%) | | |
|---|---|---|---|
| | Examples 1 | Examples 2 | Examples 3 |
| Drug Loading | | | |
| Doxycycline Hyclate | 16.8 | 16.8 | 17.2 |
| Hydroxypropylmethyl-cellulose | 6.5 | 6.5 | 6.7 |
| Sugar Spheres | 54.6 | 54.6 | 55.9 |
| Polyethylene Glycol 400 | 1.9 | 1.9 | 2 |
| Talc | 1.9 | 1.9 | 2 |
| Purified Water | q.s | q.s | q.s |
| Modified Release Coating | | | |
| Methacrylic acid Copolymer (Type C) | 10.0 | 8.19 | 8.8 |
| Hypromellose 3 Cps (Methocel E3LV) | 5 | 4.0 | 4.4 |
| Talc | 3 | 0.3. | 2.7. |
| Acetone | q.s. | q.s. | q.s |
| Water | q.s. | q.s. | q.s. |
| Lubrication | | | |
| Water | q.s. | 0.28 | 0.3 |
| Total Weight | 100 | 100 | 100 |
| Encapsulation | | | |
| Capsule shell size '1' (No.) | 1 | 1 | 1 |

Procedure for manufacturing of doxycycline hyclate modified release dosage form

A) Preparation of Drug solution

Doxycline solution was prepared comprising of doxycycline, one or more hydrophilic polymer, or other pharmaceutically acceptable excipients at a temperature above 18° C. and below 18° C.

Note: It was found that doxycycline solution if prepared above 18° C. leads to formation of hydrolytic impurity which does not meet pharmacopoeial acceptable limits.

Table 2 shows the impurity levels of formulation prepared in different conditions.

TABLE 2

| | Parameter 4-epidoxycycline (%) | |
|---|---|---|
| Time | Room temperature | Cool condition (14° C. ± 4° C.) |
| Initial | 0.08 | 0.03 |
| 24 hours | 0.19 | 0.03 |

B) Drug layering:
Drug solution as prepared in step A was layered onto sugar spheres.

C) Release layer
Mixture of methacrylic acid copolymer and hypromellose were prepared in given solvents to form a mixture, and to this talc was added and mixed well.
This mixture is sprayed onto drug coated pellets of Step B.

D) Lubrication & filling
The pellets of step C were lubricated with talc in blender and filled in HPMC capsule "size 1".

Example 4

The in vitro release study for the examples 1, 2 and 3 were carried out in changeover media. It was performed by using USP apparatus I (Basket) with 50 RPM and the dissolution methodology includes change over mediums i.e., acid stage followed by buffer stage. Table 3 shows dissolution profile of example 1, 2, 3 and ORACEA®.

First the in vitro dissolution was carried out in acid stage (750 ml of 0.1N HCl solution, USP Type 1 apparatus at a speed of 50 rpm and 37° C.) till 30 minutes. After 30 minutes of in vitro dissolution of the same composition which is used in acid stage was carried out in buffer stage (950 ml of phosphate buffer solution (pH 6.0), USP Type 1 apparatus at a speed of 50 rpm and 37° C.).

FIG. 1 shows the in vitro release profile of composition of examples 1, 2 & 3 carried out in change over media in comparison with ORACEA®.

TABLE 3

Dissolution profile of examples 1, 2 & 3 (changeover media)

| Time point | % Drug release | | | |
|---|---|---|---|---|
| (Minutes) | Example 1 | Example 2 | Example 3 | ORACEA ® |
| Acid Stage | | | | |
| 30 | 1 | 2 | 3 | 74 |
| Acid + Buffer stage | | | | |
| 30 | 1 | 2 | 3 | 74 |
| 35 | 3 | 7 | 6 | 74 |
| 45 | 41 | 56 | 48 | 76 |
| 60 | 93 | 93 | 98 | 93 |

Example 5

The in vitro release study for the example 3 was carried out in 950 ml of 0.1N HCl media. It was performed by using USP apparatus I (Basket) with 50 rpm. The dissolution data is given in Table 4.

TABLE 4

Dissolution Data of example 5 (0.1N HCl Media)

| Time point | % Drug release |
|---|---|
| 15 mins | 1 |
| 30 mins | 4 |
| 45 mins | 20 |
| 60 mins | 49 |

Example 6

The in vitro release study for the example 3 was carried out in 950 ml of acetate buffer solution (pH 4.5), USP Type 1 apparatus at a speed of 50 rpm and 37° C. The dissolution data is given in Table 5.

Figure 2:
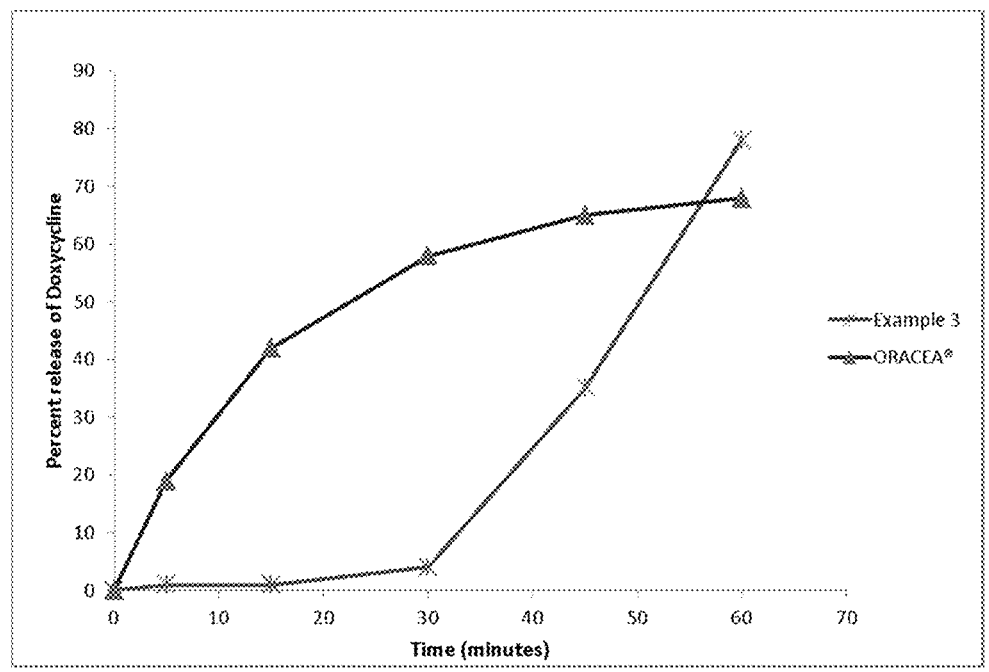
FIG. 2 shows in vitro release profile of Example 3 and ORACEA® in acetate buffer—pH 4.5.

FIG. 2 shows the in vitro release profile of composition of example 3 carried out in acetate buffer solution (pH 4.5) in comparison with ORACEA®.

TABLE 5

Dissolution Data of example 6 [acetate buffer solution (pH 4.5)]

| Time point | % drug release | | | |
|---|---|---|---|---|
| | Example 1 | Example 2 | Example 3 | ORACEA ® |
| 5 mins | 0 | 1 | 1 | 19 |
| 15 mins | 0 | 1 | 1 | 42 |
| 30 mins | 2 | 3 | 4 | 58 |
| 45 mins | 21 | 42 | 35 | 65 |
| 60 mins | 72 | 89 | 78 | 68 |

Example 7

A single center, open-labeled, balanced, randomized, 3-treatment, 3-period, 6-sequence, single-dose, crossover, comparative oral bioavailability study was conducted in 52 healthy adult volunteers.

The treatments administered in the study were composition of example 3 under the fasting condition (Treatment A), composition of example 3 under the fed condition (Treatment B) and ORACEA under the fasting condition (Treatment C). [ORACEA® (Doxycycline, USP) Capsules 40 mg, capsules of Galderma Laboratories, L.P., USA, Batch No. 1300342A, Expiry date: January 2016]

The subjects were fasted overnight for at least 10 hours before receiving a single dose of either composition of example 3 or ORACEA for Treatment A and C.

In Treatment B, the subjects were fasted overnight for at least 10 hours before receiving an FDA-standardized high-fat, high-calorie breakfast (800-1000 kcal) (FDA Guidance 2002), followed by administration of a single dose of composition of example 3.

A washout period of 7 days was maintained between the dosing of investigational products in consecutive study periods. Blood samples were collected to determine the plasma concentrations of doxycycline before dosing (pre-dose) and at 0.5, 0.75, 1, 1.33, 1.67, 2, 2.5, 3, 3.5, 4, 4.5, 5, 5.5, 6, 7, 8, 12, 16, 24, 48 and 72 hours after dosing.

The concentrations of doxycycline in plasma were determined by using a validated LC/MS-MS method.

The pharmacokinetic (PK) parameters $C_{max}$, $AUC_{0-t}$, $AUC_{0-inf}$, % Residual area, $T_{lag}$, $T_{max}$, $t_{1/2}$ and $K_{el}$ were calculated using a non-compartmental analysis (NCA) model.

The primary PK parameters, $C_{max}$, $AUC_{0-t}$, $AUC_{0-inf}$ were tested statistically for the effects of period, treatment, sequence and subject nested within sequence using the mixed-effect analysis of variance (ANOVA) method.

The geometric least squares means of $C_{max}$, $AUC_{0-t}$, $AUC_{0-inf}$ derived from the ANOVA were compared for bioequivalence under the fasting state and the food-effect and presented in terms of 90% confidence intervals of the test product (composition of example 3) to the comparator product (ORACEA) ratios.

The comparisons of interest were Treatment A vs. C for the bioequivalence assessment under fasting condition and Treatment B vs A for the food-effect and Treatment B vs. C.

Figure 3:
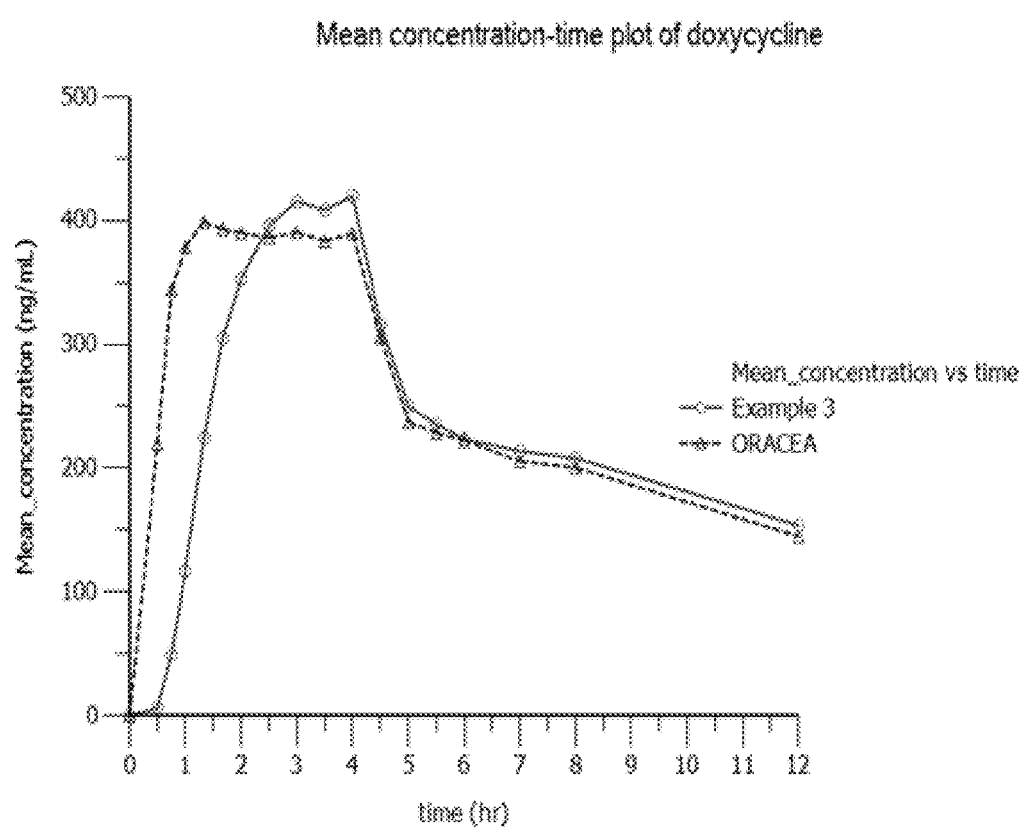
FIG. 3 A. shows 12-hour Mean plasma doxycycline concentration—Time profile of Example 3 administered to 52 subjects in fasting state.

At the end of the study following parameters are evaluated:
  a. Plasma concentration profile of Doxycyline v. time
  b. Bioequivalence study v. ORACEA® capsules
  c. Food effect study and
  d. dC/dT evaluation a. Plasma Concentration Profile of Doxycyline v. Time The plasma concentration of Doxycyline from Example 3 v. time was plotted for 12 hrs and 72 hrs respectively. FIG. 3 A. shows 12-hour mean plasma doxycycline concentration-time profile and FIG. 3 B. shows 72-hour mean plasma doxycycline concentration-time profile of example 3 administered to 52 subjects in fasting state.

The plasma concentration of example 3 vis-à-vis ORACEA® for initial time point up to 60 minutes is shown Table 6.

TABLE 6

| Time points (mins) | Plasma concentration (ng/ml/hr) | |
|---|---|---|
| | Example 3 | ORACEA® |
| 0 | 0 | 0 |
| 30 | 6.57 | 219 |
| 45 | 49.75 | 344 |
| 60 | 117.03 | 378 | b. Bioequivalence Study v. ORACEA® Capsules

It was observed that the example 3 and ORACEA® 40 mg capsules met the bioequivalence criteria as of 90% confidence intervals of Cmax and AUC parameters were within the acceptance range of 80.00% to 125.00%, in fasting conditions.

TABLE 7

| | Bioequivalence study | | |
|---|---|---|---|
| PK Parameters | Treatment A Example 3 (Fasting) | Treatment B Example 3 (Fed) | Treatment C ORACEA® 40 mg-Fasting |
| $C_{max}$ | 473.65 ± 178.79 | 325.32 ± 75.66 | 466.40 ± 156.90 |
| $AUC_{0-t}$ | 6109.48 ± 1703.82 | 5443.45 ± 1209.17 | 6239.96 ± 1538.03 |
| $AUC_{0-inf}$ | 6448.19 ± 1768.20 | 5780.34 ± 1269.96 | 6561.49 ± 1602.90 |
| $Tlag^a$ (hr) | 0.495 | 2.00 | 0.00 |
| | (0.00-0.999) | (0.501-3.50) | (0.00-0.00) |
| $Tmax^a$ (hr) | 2.99 | 5.49 | 1.99 |
| | (0.745-4.00) | (2.49-7.00) | (0.744-4.11) |
| $T_{1/2\ el}$ (hr) | 16.48 ± 3.40 | 16.50 ± 3.26 | 16.28 ± 3.87 |

$^a$Median (Min-Max)

c. Food Effect Study

The composition of example 3 was evaluated for its food effect vis-à-vis ORACEA®. The composition of example 3 exhibited a food effect of about 31% in $C_{max}$ and further showed reduction of about 31% in food effect when compared to food effect of ORACEA®. The results are shown in Table 8.

d. dC/dT Evaluation

The rate of change of doxycycline plasma concentration during the time period of $T_{0\ mins}$-$T_{60\ mins}$ was tabulated in Table 9. The rate of change of doxycycline plasma concentration during the time period of $T_{0\ min}$-$T_{60\ mins}$ of example 3 was less than 80% of rate of change of doxycycline plasma concentration during the time period of $T_{0\ min}$-$T_{60\ mins}$ of ORACEA®. The rate of change of doxycycline plasma concentration during 0-1 hrs of example was 117.03 ng/ml/hr and ORACEA® was 378 ng/ml/hr.

Calculation of dC/dT for example 3:
Plasma Concentration$_{T\ 2}$: 117.303 ng/ml
Plasma Concentration$_{T\ 1}$: 0 ng/ml
Time point$_2$: 1 hr
Time point$_1$: 0 hr $$dC/dT = \frac{(\text{Plasma Concentration}_{T2} - \text{Plasma Concentration}_{T1})}{(\text{Time point}_2 - \text{Time point}_1)}$$

$$dC/dT = \frac{(117.03-0)}{(1-0)}$$

$$dC/dT = 117.303 \text{ ng/ml/hr}$$

Calculation of dC/dT for ORACEA®:
Plasma Concentration$_{T\ 2}$: 378 ng/ml
Plasma Concentration$_{T\ 1}$: 0 ng/ml
Time point$_2$: 1 hr
Time point$_1$: 0 hr $$dC/dT = \frac{(\text{Plasma Concentration}_{T2} - \text{Plasma Concentration}_{T1})}{(\text{Time point}_2 - \text{Time point}_1)}$$

TABLE 8

Food effect
The following table lists the food effect values of composition of Example 3 and ORACEA®

| | | | Food Effect | | Reduction of Food |
|---|---|---|---|---|---|
| PK Parameters | Example 3 (Fasting) | Example 3 (Fed) | Example 3 | ORACEA® Disclosed in label | Effect of Example 3 compared to Food Effect of ORACEA® (%) |
| Cmax | 473.65 | 325.23 | 31.31% | 45% | 30.42% |
| $AUC_{0-t}$ | 6109.48 | 5443.45 | 10.90% | 22% | 50.45% |
| $AUC_{0-inf}$ | 6448.19 | 5780.34 | 10.35% | 21% | 50.71% |

-continued $$dC/dT = \frac{(378-0)}{(1-0)}$$

$$dC/dT = 378 \text{ ng/ml/hr}$$

TABLE 9 dC/dT values: Change in Doxycline
concentration as a function of time

| Time (Hrs.) | Example 3 | ORACEA ® |
|---|---|---|
| 0.0 to 1 | 117.03 ng/ml/hr | 378 ng/ml/hr |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A modified release oral composition comprising:
   i. about 30 to less than about 50 mg of doxycycline, based on the equivalent weight of doxycycline base;
   ii. one or more water soluble and insoluble polymers; and
   iii. one or more pharmaceutically acceptable excipients;
   wherein said composition is free of any immediate release component;
   wherein the doxycycline is in an amount of about 15-20% w/w, the water soluble and insoluble polymers are in an amount of about 10-18% w/w, and the pharmaceutically acceptable excipients are in an amount of about 1-20% w/w, based on the total weight of the composition; and
   wherein said composition has dC/dT value of less than about 80% of the dC/dT value provided by the commercially available 40 mg doxycycline composition, measured in a single dose human pharmacokinetic study in a fasting state and in a time period of $T_0$ min to $T_{60}$ mins.

2. The composition of claim 1, wherein said doxycycline is an acid addition salt of doxycycline.

3. The composition of claim 2, wherein said acid addition salt of doxycycline is doxycycline hyclate.

4. The composition of claim 3, wherein said doxycycline hyclate is present in an amount of about 46 mg.

5. The composition of claim 1, wherein said composition exhibits a reduced food effect selected from the group consisting of an AUC of less than about 15% and a $C_{max}$ of less than about 40% upon oral administration to a human.

6. The composition of claim 1, wherein said composition provides a reduced food effect whereby both AUC and a $C_{max}$ are lower than the food effect of commercially available 40 mg doxycycline compositions by at least about 15%.

7. The composition of claim 1, where said composition upon oral administration in a fasting state exhibits bioequivalence to a commercially available 40 mg doxycycline composition and wherein said bioequivalence is established by:
   a. a 90% Confidence Interval for mean $AUC_{(0-t)}$, which is between 80% and 125%,
   b. a 90% Confidence Interval for mean $AUC_{(0-\infty)}$, which is between 80% and 125%, and
   c. a 90% Confidence Interval for mean $C_{max}$, which is between 80% and 125%.

8. The composition of claim 1, wherein said doxycycline is present in an amount of about 30 to about 45 mg, based on the equivalent weight of doxycycline base.

9. The composition of claim 1, wherein said doxycycline is present in an amount of about 35 to about 45 mg, based on the equivalent weight of doxycycline base.

* * * * *